US012485244B2

(12) United States Patent
Berlin

(10) Patent No.: US 12,485,244 B2
(45) **Date of Patent: *Dec. 2, 2025**

(54) NASOPHARYNGEAL AIRWAY DEVICE

(71) Applicant: NPA MEDICAL, LLC, Edgewater, MD (US)

(72) Inventor: Andrew Berlin, Davidsonville, MD (US)

(73) Assignee: NPA MEDICAL, LLC, Edgewater, MD (US)

( * ) Notice: Subject to any disclaimer, the term of this patent is extended or adjusted under 35 U.S.C. 154(b) by 1025 days.

This patent is subject to a terminal disclaimer.

(21) Appl. No.: 17/316,513

(22) Filed: May 10, 2021

(65) Prior Publication Data

US 2021/0260325 A1 Aug. 26, 2021

Related U.S. Application Data

(63) Continuation of application No. 16/139,165, filed on Sep. 24, 2018, now Pat. No. 11,000,661.

(51) Int. Cl.
*A61M 16/06* (2006.01)
*A61M 16/08* (2006.01)

(52) U.S. Cl.
CPC ..... *A61M 16/0666* (2013.01); *A61M 16/0816* (2013.01)

(58) Field of Classification Search
CPC ....... A61B 5/097; A61B 5/6819; A61B 5/682; A61M 16/0003; A61M 16/0078;
(Continued)

(56) References Cited

U.S. PATENT DOCUMENTS 3,867,946 A * 2/1975 Huddy .............. A61M 16/0666 128/207.18
3,915,173 A 10/1975 Brekke
(Continued)

FOREIGN PATENT DOCUMENTS

GB 2 498 275 A 9/2012
WO 2013192121 A1 12/2013
WO 2016034572 A1 3/2016

OTHER PUBLICATIONS

Written Opinion of the International Searching Authority in International Application No. PCT/US19/52191, mailed Dec. 10, 2019, 11 pgs.

(Continued)

*Primary Examiner* — Annette Dixon
(74) *Attorney, Agent, or Firm* — Greenberg Traurig, LLP

(57) ABSTRACT

A nasopharyngeal airway device for receiving a nasal cannula is provided. The device has a flexible tube having first and second open ends and a flexible receptacle open at its upper end and integral with the flexible tube first open end. The flexible receptacle has a diameter greater than a diameter of the flexible tube and contains a lower end opening that communicates with the flexible tube first open end and opposed recesses arranged at an upper edge thereof and configured to receive and retain a nasal cannula. Preferably, the receptacle further includes a bottom wall containing the lower end opening and side wall containing the recesses. When the flexible tube second open end is inserted into a nasal passage of a patient, tubing of a nasal cannula is arranged in the recesses to deliver oxygen to the patient via the receptacle and the flexible tube.

19 Claims, 2 Drawing Sheets

(58) Field of Classification Search
CPC .............. A61M 16/04; A61M 16/0431; A61M 16/0461; A61M 16/0463; A61M 16/0488; A61M 16/049; A61M 16/0493; A61M 16/0495; A61M 16/06; A61M 16/0666; A61M 16/0672; A61M 16/0683; A61M 16/0816; A61M 16/0833; A61M 16/085; A61M 16/10; A61M 16/101; A61M 16/108; A61M 16/16; A61M 2202/0007; A61M 2202/0208; A61M 2202/025; A61M 2202/03; A61M 2205/32; A61M 2210/0618; A61M 2210/065; A61M 2210/1053; A61M 2230/005; A61M 2230/432; A61M 25/0023; A61M 31/00; A61M 16/0051; A61M 16/0409; A61M 16/0434; A61M 16/0484; A61M 16/0486; A61M 16/08; A61M 2025/022; A61M 2202/0225; A61M 2207/00; A61M 2210/1028; Y10S 128/912
See application file for complete search history.

(56) References Cited

U.S. PATENT DOCUMENTS

| | | | | |
|---|---|---|---|---|
| 4,328,797 | A * | 5/1982 | Rollins, III | A61M 16/06 128/912 |
| 4,821,715 | A * | 4/1989 | Downing | A61M 16/0461 128/207.18 |
| 7,171,962 | B1 * | 2/2007 | Bloem | A61M 16/04 128/207.14 |
| 7,918,227 | B1 * | 4/2011 | Phythyon | A61M 16/0461 128/207.14 |
| 8,220,461 | B1 * | 7/2012 | Guerra | A61M 16/0493 128/207.14 |
| 8,485,194 | B2 * | 7/2013 | Guerra | A61M 16/0486 128/207.14 |
| D695,390 | S | 12/2013 | Bruggeman et al. | |
| 9,302,064 | B2 * | 4/2016 | Hussain | A61B 5/097 |
| 11,000,661 | B2 * | 5/2021 | Berlin | A61M 16/0461 |
| 11,241,552 | B2 * | 2/2022 | Thomas | A61M 16/049 |
| 2001/0035185 | A1 * | 11/2001 | Christopher | A61M 16/0683 128/200.24 |
| 2005/0011524 | A1 | 1/2005 | Thomlinson et al. | |
| 2013/0239970 | A1 * | 9/2013 | Pizzini | A61M 16/0463 128/207.14 |
| 2014/0275784 | A1 | 9/2014 | Joyce | |
| 2016/0022941 | A1 * | 1/2016 | Ozenne | A61M 16/0486 128/207.18 |
| 2016/0296720 | A1 | 10/2016 | Henry et al. | |
| 2020/0282164 | A1 | 9/2020 | Thomas | |
| 2024/0066246 | A1 * | 2/2024 | Slaughter | A61M 16/085 |

OTHER PUBLICATIONS

European Patent Office, Extended Search Report issued in Application No. 19867811.2, dated May 23, 2022, 6 pgs.
Office Action from Canadian application No. 3,155,827, dated Feb. 21, 2024, 4 pp.
Office Action from Chinese application No. 201980075963.9, dated Nov. 16, 2023, 12 pp.

* cited by examiner

NASOPHARYNGEAL AIRWAY DEVICE

CROSS REFERENCE TO RELATED APPLICATION

This application is a continuation of and claims the benefit of U.S. patent application Ser. No. 16/139,165, filed on Sep. 24, 2018 (now granted as U.S. Pat. No. 11,000,661), the entire contents of each of which are hereby incorporated by reference in their entirety.

BACKGROUND OF THE DISCLOSURE

The present disclosure relates to a nasopharyngeal airway device and more specifically to a nasopharyngeal airway device that is adapted for receiving and retaining a nasal cannula.

A nasopharyngeal airway (NPA), also known as a nasal trumpet, is a type of airway adjunct used for treating soft tissue upper airway obstruction. NPAs are pliable, hollow cylinders made of soft plastic or rubber in variable lengths and diameters. The NPA extends through nasal passages to the posterior pharynx and beyond the base of the tongue. It typically has a flared end flange that prevents the outside end from passing beyond the nares and becoming lost inside the patient's nose, mouth, or further into the lungs or GI tract.

In a semi-conscious or unconscious patient, the jaw muscles commonly relax and allow the tongue to slide back and obstruct the airway. This obstruction makes airway management necessary, and an NPA is one of the available tools for relieving the airway obstruction. It is tolerated by most patients, even those who are conscious, and might be better tolerated in the lightly anesthetized patient as compared to an oropharyngeal airway (OPA). In cases of oropharyngeal trauma, a nasal airway is often preferable to an oral airway.

Supplemental oxygen is almost always used when an NPA is in place. The patient in the hospital setting with an NPA in place may be semi-conscious or unconscious as a result of sedation administered as part of a medical/surgical procedure which results in reduced ventilation, often requiring that supplemental oxygen be provided to maintain adequate patient oxygenation.

The most common method of delivering supplemental oxygen to the patient with an NPA is via a nasal cannula. A major benefit of using a nasal cannula with the NPA is that the same nasal cannula can be used for a period of time even after the NPA is removed but while the patient still requires supplemental oxygenation. This reuse of the nasal cannula results in significant cost savings. With the NPA, the nasal cannula is used with either one or both cannula prongs arranged inside the flange portion of the NPA.

The current problem when using a nasal cannula with an NPA is that the NPA is not specifically designed for either the one-pronged or two-pronged nasal cannula approach. The nasal prongs of a typical two-pronged nasal cannula do not simultaneously fit unencumbered inside the flange of an NPA, nor can the cannula be easily secured to the NPA flange, resulting in decreased oxygen intake, wasted oxygen and issues with maintaining a connection between the cannula and NPA. The main problem is that the flange of an NPA was designed solely as a safety mechanism to prevent the loss of the proximal end of the NPA from going further into the nose.

Further, when both nasal cannula prongs are arranged inside of the NPA flange, the prongs are too long relative to the depth of the flange resulting in a very poor fit. The prong(s) may then bend or be pushed up directly against the flange wall limiting oxygen flow. Frequently because of the poor fit, the nasal cannula prongs dislodge from the inside of the flange.

When only a single nasal cannula prong is used with an NPA, the other prong does not direct oxygen through the open channel of the NPA, but rather blows oxygen around the nose and mouth of an obstructed airway. Therefore, potentially half of the oxygen is being wasted to the ambient air, and the oxygen flow rate that is set at the flowmeter may be significantly different than what is actually delivered to the patient through the open NPA. This difference may be compensated for to a certain extent by increasing the oxygen flow rate resulting in significant waste of the supplemental oxygen. In addition, the single nasal cannula prong that is arranged inside of the NPA flange may rub directly against the flange and become partially or fully obstructed. The oxygen then escapes through the path of least resistance, which is the prong outside of the NPA.

Currently there is no ideal way to attach a nasal cannula directly to a standard NPA. The rounded plastic tubing of the nasal cannula adjacent to the prongs rolls on the outside of the NPA flange causing the cannula prongs to frequently dislodge from the inside of the flange. It is often necessary to either pull the nasal cannula neck strap very tight around the face to keep the cannula prongs in place, and/or use significant amounts of tape to hold it in place. Even these strategies have retention issues, and tightening nasal cannula straps around the head and face can be very uncomfortable for a patient waking up from sedation.

SUMMARY OF THE DISCLOSURE

Accordingly, it is an object of the present disclosure to provide a nasopharyngeal airway device for receiving a nasal cannula. The device includes a flexible tube having first and second open ends and a flexible receptacle open at its upper end and integral with the flexible tube first open end. The flexible receptacle has a diameter greater than a diameter of the flexible tube and contains a lower end opening that communicates with the flexible tube first open end and opposed recesses arranged at an upper edge thereof and configured to receive and retain a nasal cannula. Preferably, the receptacle further includes a bottom wall containing the lower end opening and side wall containing the recesses. When the flexible tube second open end is inserted into a nasal passage of a patient, tubing of a nasal cannula is arranged in the recesses to deliver oxygen to the patient via the receptacle and the flexible tube.

In a separate embodiment, the opposed recesses include openings and slits extending from the opposed recess openings to an upper edge of the receptacle. In another embodiment, the opposed recesses have a U-shape configuration. In yet another embodiment, the bottom or side wall includes a synthetic material adjacent to the opposed recesses for retaining nasal cannula tubing.

BRIEF DESCRIPTION OF THE FIGURES

Other objects and advantages of the disclosure will become apparent from a study of the following specification when viewed in the light of the accompanying drawing, in which.

DETAILED DESCRIPTION

Figure 1:
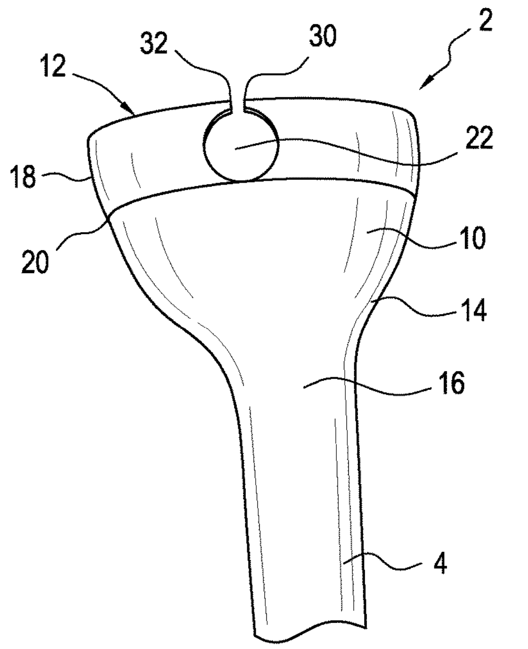
FIG. 1 is a side view of the nasopharyngeal airway device according to the present disclosure.
Figure 5:
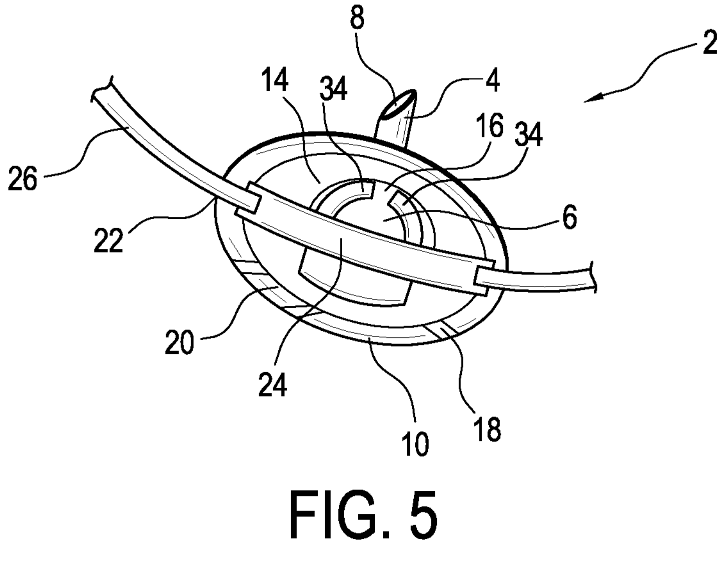
FIG. 5 is a top view of the device having a nasal cannula connected therewith.

Referring to FIGS. 1 and 5, there is shown a preferred embodiment of the nasopharyngeal airway device configured to receive a nasal cannula. For remaining embodiments, like numbers indicate like parts throughout the views. The device 2 has a flexible tube 4 having a first open end 6 and a second open end 8 and a flexible receptacle 10 integral with the flexible tube first open end and having an open upper end 12. The flexible receptacle has a diameter greater than a diameter of the flexible tube and includes a bottom wall 14 containing an opening 16 that communicates with the flexible tube first open end 6 and an annular side wall 18 extending from an outer edge 20 of the bottom wall and containing opposed recesses 22 configured to receive and retain a nasal cannula. The recesses have a U-shape configuration and terminate in slits 30 that extend from the opening of the recesses to the upper edge 32 of the receptacle providing further retention of a nasal cannula arranged within the recesses. The side wall 18 of the embodiment of FIG. 1 is upright and extends vertically from the outer edge 20 of the bottom wall. It will be understood by those of ordinary skill in the art that the side wall could extend outwardly from the outer edge of the bottom wall at numerous angles including an angle greater than the angle of the bottom wall and/or consistent with the angle of the bottom wall. It will also be understood by those with skill in the art that the configuration of the opposed recesses could differ so long as the recess is configured to receive and retain a nasal cannula.

Preferably, the receptacle 10 has a greater diameter at its open upper end 12 than at the bottom wall opening 16. Though the embodiments disclosed herein show a receptacle with a continuously and uniformly widening diameter from the bottom wall toward the open upper end, it will be understood by those with skill in the art that receptacles could have different configurations that include a greater or lesser slope from the bottom wall to the open upper end so long as the diameter of a portion of the receptacle is greater than the diameter of the flexible tube 4.

Figure 2:
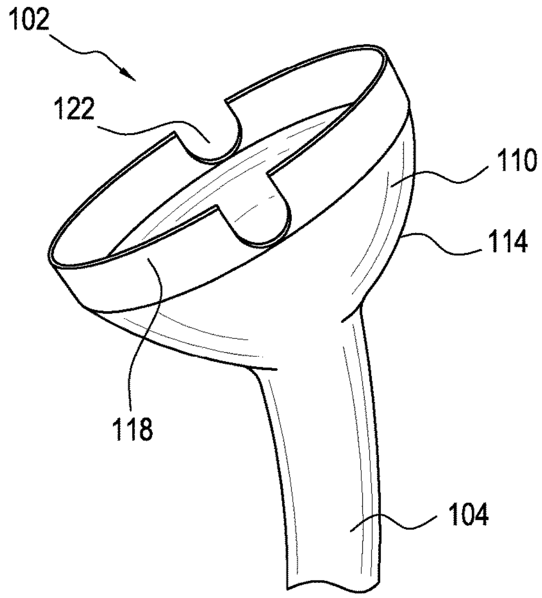
FIG. 2 is a perspective view of second embodiment of the device according to the present disclosure.

FIG. 2 shows a second embodiment of the device 102 which also has a flexible tube 104, a receptacle 110 having a bottom wall 114, an annular side wall 118, and opposing recesses 122. As with the embodiment of FIG. 1, the recesses have a U-shape configuration. However, this embodiment does not have slits that extend from the opening of the recesses to an upper edge of the receptacle, but rather is open at the upper edge.

Figure 3:
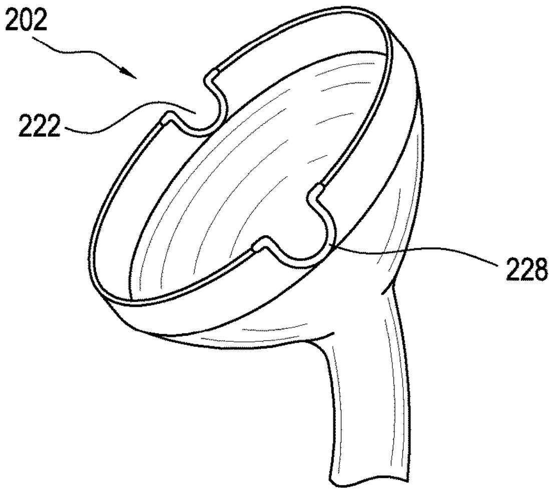
FIG. 3 is a perspective view of a third embodiment of the device according to the present disclosure.

The embodiment of device 202 of FIG. 3 includes nearly identical elements of the embodiment of FIG. 2 except that it also includes synthetic material 228 adjacent to the U-shape recesses 222. The synthetic material might, for instance, be a rubber that will grip and provide improved retention of a nasal cannula when it is pressed against the opposing recesses.

It will be understood by those of skill in the art that the embodiments described above are not exhaustive of the configuration of receptacles or opposed recesses of the device but rather are examples of how the receptacles and recesses could be configured to retain a nasal cannula. Further, it is contemplated by this disclosure that the receptacle of the device has a depth great enough so that the prongs 34 of a nasal cannula can be retained within the receptacle without the prongs 34 being significantly pushed against or encumbered by the bottom or side wall of the receptacle. Further, it is preferable for the receptacle to have an oval shape, as shown in FIG. 5, wherein the longest dimension of the receptacle is between the two recesses.

Figure 4:
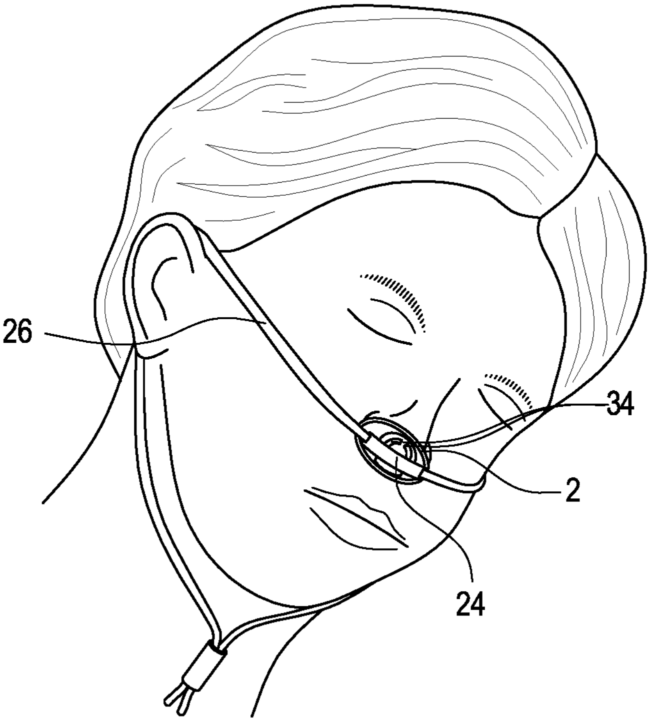
FIG. 4 shows the device inserted into the nasal cavity of patient and connected with a nasal cannula.

Referring now to FIGS. 4 and 5, the process by which the device is used will be described. FIG. 4 shows the device 2 of FIG. 1 inserted into the nasal passage of a patient and FIG. 5 shows a top view of the device 2 having an outlet 24 of a nasal cannula 26 connected therewith. When the flexible tube second open end 8 is inserted into a nasal passage of a patient, the outlet 24 of the nasal cannula 26 is arranged in the receptacle recesses 22 and oxygen is delivered to the patient via the receptacle opening 16, first open end 6, flexible tube 4 and second open end 8. The flexible tube second open end 8 is beveled to prevent it from being obstructed when placed within the nasal passage, allowing oxygen to flow more freely into the patient.

Although the above description with reference to particular embodiments, it is to be understood that these embodiments are merely illustrative of the principles and applications of the present disclosure. It is therefore to be understood that numerous modifications may be made to the illustrative embodiments and that other arrangements may be devised and employed without departing from the spirit and scope of the present disclosure.

What is claimed is:

1. A nasopharyngeal airway device for receiving a nasal cannula, comprising:

(a) a flexible tube having first and second open ends defining an airway, said first open end being positioned proximate to one of a user's nasal passages at the entry to one of the user's nostrils, said second open end opposite said first open end, said second end being sized and positioned at the entry to one of the user's nostrils and subsequently into said user's nasal passage such that the said second end is configured for positioning proximate to said user's pharynx; and (b) an open flexible receptacle having an inner end integral with said flexible tube first open end without obstruction to the flow of fluid, said open flexible receptacle having an outer end with a diameter that is substantially greater in size than the airway diameter of said flexible tube, said open flexible receptacle including:

(1) an inner receptacle portion communicating directly with said flexible tube first open end; and (2) an outer receptacle portion communicating directly with said inner receptacle portion, said outer receptacle portion including at least one recess arranged within said outer receptacle portion, wherein said at least one recess alone is configured to receive and removably restrain an outlet of the nasal cannula from which at least one nasal prong emanates, said removable retention of the outlet of the nasal cannula within said outer receptacle portion serving to maintain the position of said at least one nasal prong emanating from the outlet of the nasal cannula positioned within said open flexible receptacle, to convey oxygen from said nasal cannula at a position between said inner and outer receptacle portions, to facilitate the efficient and consistently secure conveyance of oxygen from said nasal cannula, through said at least one nasal prong, whereby the entireties of said flexible tube and said open flexible receptacle form a single integral nasopharyngeal airway device allowing oxygen to flow freely and unobstructed from said inner receptacle portion of said open flexible receptacle to said first open end of said flexible tube and in turn to said second open end of said flexible tube, wherein said second open end of said flexible tube is beveled and positioned proximate to the user's pharynx.

2. The nasopharyngeal airway device of claim 1, wherein said outer receptacle portion comprises an annular side wall containing said at least one recess.

3. The nasopharyngeal airway device of claim 1, wherein said inner receptacle portion has an inner receptacle diameter that is smaller than an outer receptacle diameter of the outer receptacle portion.

4. The nasopharyngeal airway device of claim 1, wherein said at least one recess comprises an opening and a slit.

5. The nasopharyngeal airway device of claim 1, wherein said at least one recess has a U-shape configuration.

6. The nasopharyngeal airway device of claim 1, wherein said open flexible receptacle comprises a synthetic material adjacent to said at least one recess for retaining said nasal cannula.

7. The nasopharyngeal airway device of claim 1, wherein said second open end is beveled.

8. An airway device comprising:

(a) a flexible tube having first and second open ends, wherein the second open end is positioned and sized to be directly insertable into one of a user's nostrils and subsequently said user's nasal passage; and (b) an open flexible receptacle having an inner end connected to said flexible tube first open end without obstruction to the flow of fluid, said open flexible receptacle further having an outer end, said open flexible receptacle including:

at least one recess alone configured to receive an outlet of a nasal cannula, wherein the outlet of the nasal cannula further has at least one nasal prong that emanates from said outlet, said at least one recess configured to retain said at least one nasal prong proximal to or within said open flexible receptacle, whereby the entireties of said flexible tube and said open flexible receptacle form a single integral nasopharyngeal airway device allowing oxygen to flow freely and unobstructed from an inner receptacle portion of said open flexible receptacle to said first open end of said flexible tube and in turn to said second open end of said flexible tube, wherein said second open end of said flexible tube is beveled and positioned proximate to the user's pharynx.

9. The airway device of claim 8, wherein the outer end of the open flexible receptacle has a diameter greater in size than the airway diameter of the flexible tube.

10. The airway device of claim 8, wherein said open flexible receptacle comprises an annular side wall containing said at least one recess.

11. The airway device of claim 8, wherein said open flexible receptacle has an inner receptacle diameter of the inner end that is smaller than an outer receptacle diameter of the outer end.

12. The airway device of claim 8, wherein said at least one recess comprises an opening and a slit.

13. The airway device of claim 8, wherein said at least one recess has a U-shape configuration.

14. An airway device comprising:

(a) a flexible tube having first and second open ends, wherein the second open end is positioned and sized to be insertable into one of a user's nostrils and subsequently said user's nasal passage; and (b) a flexible receptacle having third and fourth open ends, said third open end of said flexible receptacle integral with said first open end of said flexible tube without obstruction to the flow of fluid, said fourth open end of said flexible receptacle having a diameter greater than a diameter of said first open end of said flexible tube, said flexible receptacle including:

at least one recess alone configured to operably receive and restrain an outlet of a nasal cannula, such that at least a portion of at least one nasal prong of said outlet of the nasal cannula is arranged proximate to said flexible receptacle, whereby the entireties of said flexible tube and said flexible receptacle form a single integral nasopharyngeal airway device allowing oxygen to flow freely and unobstructed from an inner receptacle portion of said flexible receptacle to said first open end of said flexible tube and in turn to said second open end of said flexible tube, wherein said second open end of said flexible tube is beveled and positioned proximate to the user's pharynx.

15. The airway device of claim 14, wherein said flexible receptacle comprises an annular side wall containing said at least one recess.

16. The airway device of claim 14, wherein said third open end of said flexible receptacle has a diameter that is smaller than said diameter of said fourth open end of said flexible receptacle.

17. The airway device of claim 14, wherein said at least one recess comprises an opening and a slit.

18. The airway device of claim 14, wherein said at least one recess has a U-shape configuration.

19. The airway device of claim 14, wherein the airway device comprises a nasopharyngeal airway device.

* * * * *